United States Patent [19]

Johnson et al.

[11] Patent Number: 5,132,288
[45] Date of Patent: Jul. 21, 1992

[54] **METHOD FOR CONTROLLING *SALMONELLA ENTERITIDIS* IN POULTRY**

[75] Inventors: Eric A. Johnson; Michael C. Goodnough, both of Madison, Wis.

[73] Assignee: Michael Foods, Inc., Minneapolis, Minn.

[21] Appl. No.: 515,428

[22] Filed: Apr. 27, 1990

Related U.S. Application Data

[63] Continuation-in-part of Ser. No. 387,234, Jul. 31, 1989.

[51] Int. Cl.$^5$ .................... A01N 43/54; A61K 31/505
[52] U.S. Cl. ...................................... 514/11; 514/275; 530/319; 424/116; 544/325
[58] Field of Search ................... 424/116; 514/11, 275; 530/319; 544/325

[56] References Cited

U.S. PATENT DOCUMENTS

| | | | |
|---|---|---|---|
| 2,565,057 | 10/1947 | Clough | 530/319 |
| 2,909,522 | 10/1959 | Hitchings | 544/325 |
| 3,595,956 | 7/1971 | Florestano et al. | 530/319 |
| 3,737,534 | 6/1973 | Thornmen | 514/275 |
| 3,985,873 | 10/1976 | Alvan et al. | 514/11 |
| 4,034,099 | 7/1977 | Bryan | 514/192 |
| 4,871,722 | 10/1989 | Magyar et al. | 514/157 |

FOREIGN PATENT DOCUMENTS

| | | | |
|---|---|---|---|
| 1212304 | 11/1970 | United Kingdom | 530/319 |
| 2033224 | 5/1980 | United Kingdom | 514/275 |

OTHER PUBLICATIONS

CA 77:57033g, Bertolini et al., "Potentiation of In Vitro Antibacterial Effect of Trimethoprim by the action", (1972).
CA 96:24803x, "Stabilized Opthalmic Formation"; Marsden (1982).
CA 111:239351n, "Antibiotic Drugs: Polymyxin B Sulfate Trimethoprim", (1989).
CA 97:195663h, "In Vitro Synergistic Antibacterial Activity of Trimethoprim and Furazolidone", Bhogale et al., (1982).
Preblud et al., "Bactericidal Activities of Chloramphenicol and Eleven Other Antibiotics Against Salmonella spp.", Antimicrobial Agents and Chemotherapy, Mar. 1984, pp. 327-330 (1983).
CA 98:140404h, "In Vitro Comparison of the Susceptibility of Various Bacterial Pathogens to the Comb. of Sulfamethoxyazole-Trimethoprim", Hill (1984).
CA 94:24762s, "Combined Therapy of Salmonella infection in Chickens", Seuna et al., (1981).

*Primary Examiner*—Merrell C. Cashion, Jr.
*Assistant Examiner*—Bennett Celsa
*Attorney, Agent, or Firm*—Palmatier & Sjoquist

[57] ABSTRACT

In vitro results indicate that trimethoprim may be ineffective against *S. enteritides*. However, in vivo results show that trimethoprim alone and in combination with polymyxin B sulfate is effective on *S. enteritidis* infections in poultry.

9 Claims, No Drawings

METHOD FOR CONTROLLING *SALMONELLA ENTERITIDIS* IN POULTRY

This application is a continuation-in-part of Application Ser. No. 387,234, filed Jul. 31, 1989, which is hereby incorporated by reference.

The present invention relates to methods for controlling *Salmonella enteritidis* in the test tube and in live poultry and, more particularly, to methods utilizing antimicrobial agents such as trimethoprim and polymyxin.

BACKGROUND OF THE INVENTION

Salmonella infections have been prevalent in poultry flocks for several decades. Recently, *Salmonella enteritidis* (*S. enteritidis*) infections have caused epidemics in the United States and the United Kingdom. Outbreaks of food poisoning in humans due to the consumption of grade A eggs have increased dramatically. Epidemiological and microbiological investigations have shown that the outbreaks have involved foods containing hen's eggs, and approximately 80% have been caused by *S. enteritidis*. See St. Louis, M. E. et al. 1988. *The Emergence of Grade A Eggs as a Major Source of S. enteritidis Infections.* J. Amer. Med. Assoc. 259:2103-2107 and Coyle, E. F. et al. 1988. *S. enteritidis Phase Type 4 Infection: Association with Hen's Eggs.* Lancet, Dec. 3, p. 1295-1296.

The poultry industry urgently needs to find means to control infections of poultry flocks and eggs. The gastric tract of poultry is a major reservoir of human pathogens. Feed is often the source of contamination, which leads to intestinal infection or colonization in the chicken. In turn, virulent pathogens may enter the blood and oviduct by passage through the cecal mucosa. Much effort has been concentrated on the elimination of pathogens from the environment, feeds and gastric tracts of poultry. Extensive research has been performed on providing competitive flora, referred to as the "Nurimi Concept." However, infections still persist.

In order to understand the present invention, it may be helpful to briefly review some features of bacteria and antibiotics. A bacterium is a unicellular microorganism which may exist either as a free-living organism or as a parasite. Bacteria, or a single bacterium, have a wide range of biochemical and pathogenic properties.

Bacteria may be classified according to cell wall structure into two basic groups: gram-negative bacteria and gram-positive bacteria. Gram-negative bacteria have more complex cell wall structures than gram-positive bacteria. In particular, the cell wall of gram-negative bacteria have an outer membrane, which is absent from gram-positive bacteria.

The outer membrane of a gram-negative bacterium includes inner and outer protein layers with phospholipid (a type of fat) disposed in a bilayer between the protein layers. The proteins may include matrix protein (also referred to as porin) which is transmembranal and may create pores in the membrane to allow diffusion of molecules through the outer layer. Lipoproteins may anchor the outer membrane to a peptidoglycan layer. The outer membrane, lipoprotein, peptidoglycan, and periplasmic space, which are all layers external to the inner membrane, may be referred to as the cell wall.

The outer membrane of the cell wall includes lipopolysaccharide molecules which extend from the cell wall. An outermost portion of a lipopolysaccharide molecule is referred to as an O antigen polysaccharide. O antigens are specific polysaccharide side chains and are often the major antigenic determinants in gram-negative bacteria.

The outer membrane may repel certain compounds. For instance, the lipopolysaccharide molecules are hydrophilic (water-loving). Hence, the lipopolysaccharide molecules may deter the approach of hydrophobic compounds. However, even hydrophilic compounds of a size greater than the pores created by the matrix protein may be excluded by the outer layer.

Salmonella is gram-negative group of bacteria with more than 2,000 serotypes. In biological nomenclature, Salmonella is a genus which contains only one species. The one species comprises seven subspecies. Each subspecies is divided into serovars. Serovars are further divided into serotypes. *S. enteritidis* has been identified as a serovar.

An antibiotic is a naturally produced substance which is effective in inhibiting the growth of or destroying microorganisms. Antibiotics may be produced by fungi, bacteria, or other organisms.

An antibiotic such as polymyxin may damage or kill a bacterium such as by altering its membrane permeability, impeding respiration or impairing certain transport phenomena such as electron transport of the microorganism. For example, an antibiotic may bind to the outer membrane of a bacterium and open holes in the membrane through which components of the cell may leak out, thereby killing the bacterium. In other words, the permeability of the outer and inner membranes for small-molecular weight compounds may be increased in the presence of antibiotics and the efflux of cytoplasmic components may occur.

SUMMARY OF THE INVENTION

A feature of the present invention is the provision in controlling of *S. enteritidis* in poultry, of introducing trimethoprim into the poultry.

Another feature of the present invention is the provision in controlling *S. enteritidis* in poultry, of introducing trimethoprim and polymyxin B into the poultry.

Another feature of the present invention is the provision in controlling *S. enteritidis* in poultry, of an antimicrobial mixture of trimethoprim and water.

Another feature of the present invention is the provision in controlling *S. enteritidis* in poultry, of an antimicrobial mixture of trimethoprim, polymyxin B, and water.

Another feature of the present invention is the provision in controlling *S. enteritidis*, of introducing trimethoprim into poultry 24 hours old and continuing to introduce the trimethoprim daily via the poultry's drinking water for about 15 days or until the poultry's normal intestinal flora matures.

An advantage of the present invention is the prevention of *S. enteritidis* in poultry.

Another advantage of the present invention is the removal of *S. enteritidis* from poultry.

DETAILED DESCRIPTION

1. Verification of *S. Enteritidis*

The *S. enteritidis* strains used in the in vitro and in vivo examples were obtained from the N.Y. State Health Department and were labeled as E40 and 13076 strains. The E40 strain was originally isolated from a chicken ovary. The strains were identified as being in fact *S. enteritidis* by using the Kauffmann method which uses biochemical testing to differentiate the separate species, serotypes, or serovars.

The Kauffman method recognizes that different types of bacteria have different O antigens and different H antigens. For example, *S. enteritidis* has O antigens identified by the numbers 1, 9, and 12, and H antigens identified by the letters g and m.

According to the Kauffmann method, homologous antiserum, which is commercially available, is reactive with its respective specific antigen and causes bacterial cells which have that specific antigen to agglutinate or clump together. The agglutination reaction is readily seen with the naked eye on a microscope slide. Identification of a Salmonella species is mainly based on a series of agglutination reactions. The reactions are also run alongside of known negative controls for the comparison of agglutinated cells with non-agglutinated cells.

2. Preparation of *S. Enteritidis* Cultures

The *S. enteritidis* cultures used in the in vitro and in vivo portions of the present invention were prepared by growing approximately $10^{10}$ (ten billion) cells in 10–20 ml of soy broth in 24 hours immediately prior to inoculation of either the agar plates or the live chicks. The soy broth was prepared as identified below.

3 Preparation of the Soy Broth solution for *S. Enteritidis* cultures

A one liter solution of Trypticase ® soy broth was prepared by dissolving 30 grams of the soy broth powder in one liter of purified water. The solution was mixed thoroughly and stirred until the soy broth powder was completely dissolved. The solution was then autoclaved at 121° C. for 15 minutes to sterilize the broth by killing any viable microorganisms.

The Trypticase ® soy broth is available from BBL Microbiology Systems, Becton Dickinson and Co., Cockeysville, Md. For every 30 grams, the Trypticase ® soy broth has a composition of 17.0 grams of pancreatic digest of casein, 3.0 grams of papaic digest of soybean meal, 5.0 grams of sodium chloride, 2.5 grams of dipotassium phosphate, and 2.5 grams of dextrose. Such a broth provides nutrients for the rapid reproduction or growth of *S. enteritidis*.

4. Preparation of the Reagent Antimicrobial Starting Materials

The trimethoprim and polymyxin B sulfate starting materials used in both the in vitro and in vivo testing were filter sterilized through non-pyrogenic, sterile, low protein binding, Acrodisc ® disposable filter assemblies available from Gelman Sciences, 600 S. Wagner Road, Ann Arbor, Mich. The purpose of filter sterilizing the starting materials is to remove any viable microorganisms. The starting materials were filter sterilized instead of autoclaved because trimethoprim and polymyxin B sulfate are heat sensitive.

5 Preparation of Agar Medium

Agar is a mucilaginous material used as a base for bacterial culture media and selectively allows the growth of certain types of bacteria. Agar media used in this experiment were dehydrated Bacto ® bismuth sulfite agar, dehydrated Bacto ® XLD agar, and Bacto ® Brilliant Green agar all of which were obtained from Difco Laboratories of Detroit, Mich. The Bacto ® bismuth sulfite agar is represented by Difco as being a highly selective medium for the isolation of Salmonella, especially *Salmonella typhi*. The Bacto ® XLD agar is represented by Difco as being a selective and differential primary plating medium for isolating and differentiating gram-negative enteric bacilli, especially Shigella and Providencia. The Bacto ® Brilliant Green agar is represented as being a highly selective, primary plating medium for isolating Salmonella other than *Salmonella typhi*. In less than 24 hours, an individual Salmonella cell divides a sufficient number of times and grows on the agar medium to form a mass which is perceivable to the naked eye. That mass, in biological nomenclature, is a colony.

Fecal samples were collected in pre-weighed, sterile tubes by expressing the sample from the birds' cloaca. Except when enriched, the fecal samples were diluted with 1 ml of buffered saline and dilutions thereof were streaked onto the two types of agar medium. The agar plates were then incubated for 24 hours at 37° C. By measuring the amount of fecal sample obtained, the amount of dilution with the buffer, the amount of buffer with fecal sample mix placed on the plate after the dilution, the number of colony forming units in the fecal sample may be determined from the number of colonies counted on the plate.

6. Preparation of Enrichment Broths

An enrichment broth is a liquid selective medium that directly receives an undiluted fecal sample and permits Salmonella species of the fecal sample to multiply perhaps 100–700 times over 24 hours while remaining mobile in solution. The enrichment broth simultaneously inhibits reproduction of other bacteria. In contrast, a mucilaginous material such as bismuth sulfite agar receives only liquid samples such as diluted fecal samples. Agar media does not permit movement of the bacteria, which reproduce in single locations and grow from a single *S. enteritidis* cell or "colony forming unit" to a colony that is visible to the naked eye.

The plated agar method is inaccurate when *S. enteritidis* counts are low such as when fecal samples of 0.5g or less contain five *S. enteritidis* cells or less. When the fecal samples are dispersed into a liquid medium (and hence diluted), it is often difficult to locate the five cells. Accordingly, such fecal samples are "enriched" in an enrichment broth before being plated on agar medium.

With an enrichment broth, a portion of the fecal sample is deposited into a test tube containing 10 milliliters of the broth. The solution is then stirred and incubated for 24 hours at 37° C. Over 24 hours, *S. enteritidis* cells may multiply 100–700 times. After the incubation period, the solution is stirred and a loopfull of the solution is streaked onto the bismuth sulfite and XLD agar medium and incubated another 24 hours. The agar plates are then observed to determine the presence or absence of *S. enteritidis* colony forming units. The observation of even one *S. enteritidis* colony forming unit is scored as a (+) sign in Tables 3 and 4, while the absence of any *S. enteritidis* colony forming units is identified by the (−) sign. The number of *S. enteritidis* cells per gram of fecal sample is not determinable with enrichment broths because the growth rate of the cells in the enrichment broths cannot be quantified accurately.

Bacto Selenite Cystine Broth (SC) is a selective enrichment broth that permits Salmonella species to grow while reducing growth of fecal coli and enterococci. A dehydrated Selenite Cystine enrichment broth contains the following ingredients:

| | |
|---|---|
| Bacto Tryptone | 5 g |
| Bacto Lactose | 4 g |
| Disodium Phosphate | 10 g |
| Sodium Acid Selenite | 4 g |
| L-Cystine | 0.01 g |

The Selenite Cystine Broth was prepared by suspending 23 g of the broth in one liter of distilled water. The solution was then heated to boiling to dissolve the broth. The solution was then dispensed in sterile test tubes and allowed to cool to room temperature. When cool, the test tubes were inoculated with the remainder of the fecal sample and incubated at 37° C. for about 24 hours. A loopfull of the culture was then streaked for isolation on each of the bismuth sulfite and XLD agar mediums.

Bacto Tetrathionate Broth Base (Tet) is a selective enrichment broth base that also enriches members of the Salmonella group in the isolation of these organisms from infectious material. A liter of dehydrated Bacto Testrathionate Broth Base has the following ingredients:

| | |
|---|---|
| Proteose peptone, Difco | 5 g |
| Bacto Bile Salts | 1 g |
| Sodium Thiosulfate | 30 g |
| Calcium Carbonate | 10 g |

A medium of Bacto Tetrathionate Broth Base was prepared by suspending 4.6 g in 100 ml of distilled water. The medium was heated to boiling and then cooled to room temperature. A 2 ml iodine solution, which was prepared by dissolving 6 g iodine crystals and 5 g potassium iodide in 20 ml of distilled water was added to the medium. Approximately 10 ml quantity of the medium was dispensed into sterile test tubes and inoculated with entire fecal samples. The solutions were incubated at 37° C. for 24 hours. A loopfull of the culture was then streaked for isolation on the bismuth sulfite and XLD agar mediums.

7. In vitro Testing of Trimethoprim Alone and in Combination with Polymyxin B Sulfate A solution of Trypticase ® soy broth, containing 2% agar, was prepared. The agar solution was autoclaved and subsequently given amounts of the respective antimicrobial compounds or combinations were added to give the final concentrations of the antimicrobials as noted in Tables 1 and 2. Each of the antimicrobial, soy broth agar solutions was then poured into a Petri dish and allowed to solidify at room temperature. After the antimicrobial soy agar cooled and hardened, each of plates (except for control example nos. 1 and 7) was inoculated with 0.1 ml of 24 hour culture of *S. enteritidis* by streaking the culture across the soy agar with the blade of a biological "hockey stick" which is a glass stick formed like a hockey stick. The plates were incubated at 37° C. for 24 hours, after which the agar was analyzed for *S. enteritidis* colonies. The soy agar plates of Table 2 (Examples 7-11) were incubated for 48 hours instead of 24 hours.

TABLE 1

Incubation of *S. enteritidis* for 24 Hours

| Example | Antibacterial Compound or Combination in Trypticase Soy Agar | Number of *S. enteritidis* Colony Forming Units per ml of Agar After 24 hours of Incubation |
|---|---|---|
| 1 | Control (no antibacterial compound) | $1.48 \times 10^9$ |
| 2 | Polymyxin B sulfate (1 ug/ml) | $4.7 \times 10^3$ |
| 3 | Trimothoprim (1 ug/ml) | $1.0 \times 10^9$ |
| 4 | Trimethoprim (1 ug/ml) and polymyxin B sulfate (1 ug/ml) | $1.6 \times 10^3$ |
| 5 | Trimethoprim (3.3 ug/ml) | $10^9$ |
| 6 | Trimethoprim (6.6 ug/ml) | $10^9$ |

TABLE 2

Incubation of *S. enteritidis* for 48 Hours

| Example | Antibacterial Compound or Combination | Number of *S. enteritidis* Colony Forming Units per ml of Agar after 48 hours of Incubation |
|---|---|---|
| 7 | Control (no antibacterial compound) | $6.45 \times 10^8$ |
| 8 | Polymyxin B sulfate (1 ug/ml) | $6.5 \times 10^8$ |
| 9 | Trimethoprim (6.6 ug/ml) | $5.5 \times 10^8$ |
| 10 | Trimethoprim (10 ug/ml) | $10^8$ |
| 11 | Trimethoprim (25 ug/ml) | $10^8$ |

Examples 1-11 indicate that trimethoprim may be ineffective in vitro. As shown by Examples 3, 5 and 6, *S. enteritidis* appears to be resistant at trimethoprim concentrations of 1 ug/ml, 3.3 ug/ml and 6.6 ug/ml when incubated on soy agar for 24 hours. As shown by examples 9, 10 and 11, *S. enteritidis* appears to be resistant at trimethoprim concentrations of 6.6 ug/ml, 10 ug/ml and 25 ug/ml. However, the *S. enteritidis* colonies of Examples 9, 10 and 11 were translucent, in contrast to the opaque colonies of Example 7. Hence, the colony morphology may indicate that trimethoprim may be partially affecting growth of the *S. enteritidis* cells.

8. In Vivo Testing of Trimethoprim alone and in combination with Polymyxin B Sulfate Trimethoprim alone and in combination with polymyxin B sulfate was introduced to chicks via their drinking water supply. A first group of chicks received the antimicrobial mixtures before being inoculated with *S. enteritidis* to determine whether the antimicrobial mixtures were effective in preventing infection of *S. enteritidis*. A second group of chicks received the antimicrobial mixtures after being inoculated with *S. enteritidis* to determine whether the antimicrobial mixtures were effective in removing *S. enteritidis* infections.

24 hour old Dekalb chicks were obtained from Sunnsyside Poultry Farm of Oregon, Wis. and placed individually into separate solid bottom cages.

The chicks were fed antibiotic-free feed (Ralston Purina's "Start and Grow") which was given ad libitum. Tap water and/or the antimicrobial mixtures were supplied in 8 ounce quantities in pint Mason jars and changed daily. The chicks resided in the BioTron facility at the University of Wis., Madison, which is a facility with proper containment features for working with class III pathogens.

A. Prevention of S. enteritidis in poultry

On day 1, chicks 12-19 were fed trimethoprim alone and in combination with polymixin B sulfate in concentrations as identified in Table 3. On day two, each of the chicks 12-19 was inoculated orally with a 0.5 ml solution of a 24-hour culture of E40 S. enteritidis which had an absorbence reading of $O.D._{660}0.71$ by a Spectronic ® 20 spectrophotometer available from Milton Roy Company of Rochester, N.Y. Each of the examples 12-19 represents one chick.

As shown in Table 3, fecal samples were expressed from chicks 12-19 on days 2, 6, 7, 9 and 15 after introduction into individual cages. On days 2 and 6, bismuth sulfite and XLD agar medium was used to determine the number of S. enteritidis colony forming units per gram of fecal sample. On day 7, 9 and 15 the fecal samples were placed in enrichment broths before being plated onto agar medium to determine the presence of S. enteritidis.

On day 6, the fecal sample of the trimethoprim-treated chick 18 contained less than 70 S. enteritidis cells per gram. The fecal samples of chicks 13-16, treated with trimethoprim and polymyxin B sulfate combinations, contained from about 68 to about 238 S. enteritidis cells per gram. These results are in contrast to the 70,000,000 (seventy million) S. enteritidis cells per gram of fecal sample for the untreated chick 19. Growth of S. enteritidis as even inhibited in chicks 12 and 17 where the fecal samples contained 10,000 to 1,000,000 S. enteritidis cells per gram.

Trimethoprim-treated chick 18 was apparently completely free of S. enteritidis on day 7 and continued to show negative results on days 9 and 15. Chick 13, which was treated with a minimum amount of polymyxin B sulfate (10 ug/ml) and a significant amount of trimethoprim (250 ug/ml), also was apparently completely free of S. enteritidis by day 7, and also continued to show negative results on days 9 and 15.

Chick 12 appeared to be near death on day 9 and was sacrificed. Fecal samples could not be expressed from chicks 14 and 15 on day 9, but on day 15 the expressed samples from these chicks indicated that the chicks were free of S. erteritidis. Chick 16 showed negative results on days 7 and 9 but S. enteritidis was detected on day 15. thick 17, treated with polymyxin B sulfate only, showed positive results on days 7 and 9, but was near death on day 15 and was sacrificed.

TABLE 3

GROUP I: Prevention of S. enteritidis in Poultry

| Antimicrobial Concentration In Drinking Water Supply | Number of colony forming units per gram of chick fecal sample as determined with Bismuth Sulfide and XLD agars, and presence or absence of S. enteritidis as determined with Selenite Cystine and Tetrathionate Broth enrichments on days following placement into separate cages | | | | |
|---|---|---|---|---|---|
| | Day 2 Agar | Day 6 Agar | Day 7 Enrich't | Day 9 Enrich't | Day 15 Enrich't |
| Example 12: Polymyxin B Sulfate (10 ug/ml) and Trimethoprim (100 ug/ml) | BS $2.4 \times 10^6$ XLD $1.1 \times 10^6$ | BS $1.9 \times 10^6$ XLD $1.2 \times 10^4$ | SC(+) Tet(+) | Sacrificed | — |
| Example 13: Polymyxin B Sulfate (10 ug/ml) and Trimethoprim (250 ug/ml) | BS $-3 \times 10^3$ XLD $-3 \times 10^3$ | BS $-2.3 \times 10^2$ XLD $-2.3 \times 10^2$ | SC(−) Tet(−) | SC(−) Tet(−) | SC(−) Tet(−) |
| Example 14: Polymyxin B Sulfate (50 ug/ml) and Trimethoprim (100 ug/ml) | BS $-5 \times 10^2$ XLD $-5 \times 10^2$ | BS $1.1 \times 10^2$ XLD $1.1 \times 10^2$ | SC(+) Tet(+) | * | SC(−) Tet(−) |
| Example 15: Polymyxin B Sulfate (50 ug/ml) and Trimethoprim (250 ug/ml) | BS $1.2 \times 10^6$ XLD $4.6 \times 10^5$ | BS $-2.38 \times 10^2$ XLD $-2.38 \times 10^2$ | SC(+) Tet(+) | * | SC(−) Tet(−) |
| Example 16: Polymyxin B Sulfate (100 ug/ml) and Trimethoprim (100 ug/ml) | BS $1 \times 10^2$ XLD $1 \times 10^2$ | BS $-6.8 \times 10^1$ XLD $-6.8 \times 10^1$ | SC(−) Tet(−) | SC(−) Tet(−) | SC(+) Tet(+) |
| Example 17: Polymyxin B sulfate (100 ug/ml) | BS $-8 \times 10^2$ XLD $-8 \times 10^2$ | BS $4.8 \times 10^5$ XLD $8.4 \times 10^5$ | SC(+) Tet(+) | SC(+) Tet(+) | Sacrificed |
| Example 18: | | | | | |

TABLE 3-continued

| | GROUP I: Prevention of *S. enteritidis* in Poultry | | | | |
|---|---|---|---|---|---|
| Antimicrobial Concentration In Drinking Water Supply | Number of colony forming units per gram of chick fecal sample as determined with Bismuth Sulfide and XLD agars, and presence or absence of *S. enteritidis* as determined with Selenite Cystine and Tetrathionate Broth enrichments on days following placement into separate cages | | | | |
| | Day 2 Agar | Day 6 Agar | Day 7 Enrich't | Day 9 Enrich't | Day 15 Enrich't |
| Trimethoprim (250 ug/ml) | BS $6.6 \times 10^3$ XLD $1.5 \times 10^4$ | BS $7.0 \times 10^1$ XLD $7.0 \times 10^1$ | SC(−) Tet(−) | SC(−) Tet(−) | SC(−) Tet(−) |
| Example 19: Control (250 ug/ml) | BS $5 \times 10^2$ XLD $5 \times 10^2$ | BS $7.3 \times 10^7$ XLD $7.8 \times 10^7$ | SC(+) Tet(+) | SC(+) Tet(+) | SC(+) Tet(+) |

Fecal sample could not be expressed

Each of the following examples 20–23 represents fecal sample obtained or pooled from three chicks, each of which was placed in a separate solid bottom cage. Each of the birds with the exception of the control group (example 20) was supplied with its respective antimicrobial on Day 1 and inoculated orally with 0.5 ml of an $E40$ *S. enteritidis* solution containing about $10^8$ CFU/ml.

Fecal samples were expressed from the twelve chicks on days 4, 6, 8, 1, 13, 15 and 19. *S. enteritidis* was prevented in the three chicks of example 22 which were fed the polymixin B sulfate and trimethoprim combination through day 11. On day 11, the chicks of example 22 were taken off the antimicrobials and transferred to clean cages, but maintained in close proximity with infected chicks. The chicks of example 22, as expected, tested positive for *S. enteritidis* after the antimicrobials were discontinued.

*S. enteritidis* in the chicks of example 21 was initially suppressed through at least day 8. The infection in these polymyxin B sulfate treated chicks returned on day 13 and was present at the end of the experiment on day 19.

The infection in the trimethoprim treated chicks of example 23 was present throughout the experiment. However, as indicated by the results on days 6 and 8, the infection was somewhat suppressed as the average number of colony forming units per gram in the control group ranged from 1.5 million to more than 20 million while the colony forming units of the fecal samples of example 23 ranged from 440,000 to 660,000.

Therefore, in view of examples 12–23, it is concluded that *S. enteritidis* infections are preventable in chicks where the chicks are treated with a trimethoprim and polymyxin B sulfate combination. Trimethoprim utilized alone appears to at least suppress the infection and, as indicated by example 18, may also prevent the infection.

TABLE 4

| | GROUP I: Prevention of *S. enteritidis* in Poultry | | | | |
|---|---|---|---|---|---|
| Antimicrobial Concentration in Drinking Water Supply | Number of colony forming units per gram of chick fecal sample as determined with Bismuth Sulfide, XLD, and Brilliant Green agars, and presence or absence of *S. enteritidis* as determined with Selenite Cystine and Tetrathionate Broth enrichments. | | | | |
| | Day 4 | Day 6 | Day 8 | Day 11 | Day 13 |
| Example 20 (Control) No antimicrobials | BS $2.3 \times 10^3$ XLD $1.8 \times 10^3$ BG $2.5 \times 10^3$ | BS $>10^4$ XLD $>8.00 \times 10^6$ BG $>10^4$ [$>2 \times 10^7$]* | BS $1.1 \times 10^6$ XLD $1.6 \times 10^5$ BG $1.9 \times 10^5$ [$1.5 \times 10^6$] | BS SC(+) Tet(+) XLD SC(+) Tet(+) BG SC(+) Tet(+) | BS SC(+) Tet(+) XLD SC(+) Tet(+) BG SC(+) Tet(+) |
| Example 21 Polymyxin B Sulfate (100 ug/ml) | BS $0 \times 10^2$ XLD $0 \times 10^2$ BG $0 \times 10^2$ | BS $2.4 \times 10^4$ XLD $6 \times 10^3$ BG $1.7 \times 10^4$ [$1.2 \times 10^5$] | BS 0 XLD 0 BG 0 | | BS $2.00 \times 10^6$ XLD $4.5 \times 10^5$ BG — [$4.0 \times 10^6$] |
| Example 22 Polymyxin B Sulfate (100 ug/ml) and Trimethoprim (250 ug/ml) | BS $0 \times 10^2$ XLD $0 \times 10^2$ BG $0 \times 10^2$ | BS $0 \times 10^1$ XLD $0 \times 10^1$ BG $0 \times 10^1$ [0] | BS 0 XLD 0 BG 0 | BS SC(−) Tet(−) XLD SC(−) Tet(−) BG SC(−) Tet(−) | BS SC(−) Tet(−) XLD SC(−) Tet(−) BG SC(−) Tet(−) |
| Example 23 Trimethoprim (250 ug/ml) | BS $7.8 \times 10^5$ XLD $1.9 \times 10^5$ BG $5.5 \times 10^5$ | BS $6.3 \times 10^4$ XLD $2.2 \times 10^4$ BG $3.5 \times 10^4$ [$4.4 \times 10^5$] | BS $6.6 \times 10^4$ XLD $6.1 \times 10^3$ BG $4 \times 10^4$ [$6.6 \times 10^5$] | | BS SC(+) Tet(+) XLD SC(+) Tet(+) BG SC(+) Tet(+) |
| | | | | Day 15 | Day 19 |
| Example 20 (Control) No antimicrobials | | | | BS $1.2 \times 10^4$ XLD $1.8 \times 10^4$ BG — [$4.4 \times 10^4$] | BS SC(+) Tet(+) XLD SC(+) Tet(+) BG SC(+) Tet(+) |
| Example 21 Polymyxin B | | | | | BS $1.8 \times 10^4$ |

TABLE 4-continued

GROUP I: Prevention of S. enteritidis in Poultry

| Antimicrobial Concentration in Drinking Water Supply | Number of colony forming units per gram of chick fecal sample as determined with Bismuth Sulfide, XLD, and Brilliant Green agars, and presence or absence of S. enteritidis as determined with Selenite Cystine and Tetrathionate Broth enrichments. | | |
|---|---|---|---|
| | Sulfate (100 ug/ml) | | XLD $7 \times 10^3$<br>BG $8 \times 10^3$<br>$[2.7 \times 10^4]$ |
| | Example 22 | | |
| | Polymyxin B Sulfate (100 ug/ml) and) Trimethoprim (250 ug/ml) | BS SC(−) Tet(−)<br>XLD SC(−) Tet(−)<br>BG SC(−) Tet(−) | BS SC(+)Tet(+)<br>XLD SC(+)Tet(+)<br>BG SC(+)Tet(+) |
| | Example 23 | | |
| | Trimethoprim (250 ug/ml) | BS SC(+)Tet(+)<br>XLD SC(+)Tet(+)<br>BG SC(+)Tet(+) | BS SC(+)Tet(+)<br>XLD SC(+)Tet(+)<br>BG SC(+)Tet(+) |

*Bracketed numbers represent average number of CFU/gm of fecal sample when dilution of the fecal sample is taken into account.

B. Removal of S. enteritidis from poultry 24–31

Chicks 24–31 were inoculated on day 2 with the same culture of S. enteritidis as used with chicks 12–19, but were not supplied with their respective antibacterial mixtures until day 4. Each of the examples 24–31 represents one chick.

As shown in Table 5, fecal samples were expressed from chicks 24–31 on days 3, 7, 9, 13 and 15 after introduction into individual cages. On days 3, 7, 9 and 13, agar medium was used in determining the number of S. enteritidis colony forming units per gram of fecal sample. On day 15, the fecal samples were placed into an enrichment broth for being plated onto agar medium.

Examples 24–31 indicate that it is more difficult to remove S. enteritidis infections from poultry than it is to inhibit such an infection. However, the results of days 13 and 15 show that S. enteritidis infections may be treated or controlled. For example, the S. enteritidis infection was apparently removed from chick 27 on day 15. Moreover, the infection in chick 26 was substantially controlled; its fecal sample on day 13 contained less than 180 S. enteritidis cells per gram in contrast to the 640,000 to 3,000,000 S. enteritidis per gram of the fecal sample of the untreated chick 31. Furthermore, it should be noted that chicks 25 and 26 showed at least one negative reading on day 15.

TABLE 5

GROUP II: Removal of S. enteritidis from Poultry

| Antimicrobial Concentration In Drinking Water Supply | Number of colony forming units per gram of chick fecal sample as determined with Bismuth Sulfide and XLD agars, and presence or absence of S. enteritidis as determined with Selenite Cystine and Tetrathionate Broth enrichments on days following placement into separate cages | | | | |
|---|---|---|---|---|---|
| | Day 3 Agar | Day 7 agar | Day 9 agar | Day 13 Agar | Day 15 Enrich't |
| Example 24: | | | | | |
| Polymyxin B Sulfate (10 ug/ml) and Trimethoprim (100 ug/ml) | BS $7.4 \times 10^3$<br>XLD $5.7 \times 10^3$ | BS $2.4 \times 10^3$<br>XLD $1.9 \times 10^4$ | BS $2.0 \times 10^5$<br>XLD $1.8 \times 10^5$ | Sacrificed | |
| Example 25: | | | | | |
| Polymyxin B Sulfate (10 ug/ml) and Trimethoprim (250 ug/ml) | BS $1.2 \times 10^4$<br>XLD $1.1 \times 10^4$ | BS $1.9 \times 10^4$<br>XLD $1.3 \times 10^4$ | BS $1.3 \times 10^3$<br>XLD * | BS *<br>XLD $4.3 \times 10^5$ | SC(+)<br>Tet(−) |
| Example 26: | | | | | |
| Polymyxin B Sulfate (50 ug/ml) and Trimethoprim (100 ug/ml) | BS $1.8 \times 10^4$<br>XLD $2.3 \times 10^4$ | BS $5.3 \times 10^2$<br>XLD $5.3 \times 10^1$ | BS $5.5 \times 10^2$<br>XLD * | BS $1.8 \times 10^2$<br>XLD $1.8 \times 10^2$ | SC(−)<br>Tet(+) |
| Example 27: | | | | | |
| Polymyxin B Sulfate (50 ug/ml) and Trimethoprim (250 ug/ml) | BS $3.4 \times 10^4$<br>XLD * | BS $4.9 \times 10^2$<br>XLD * | BS *<br>XLD * | BS $8.2 \times 10^2$<br>XLD 0 | SC(−)<br>Tet(−) |
| Example 28: | | | | | |

TABLE 5-continued

GROUP II: Removal of S. enteritidis from Poultry

| Antimicrobial Concentration In Drinking Water Supply | Number of colony forming units per gram of chick fecal sample as determined with Bismuth Sulfide and XLD agars, and presence or absence of S. enteritidis as determined with Selenite Cystine and Tetrathionate Broth enrichments on days following placement into separate cages | | | | |
|---|---|---|---|---|---|
| | Day 3 Agar | Day 7 agar | Day 9 agar | Day 13 Agar | Day 15 Enrich't |
| Polymyxin B Sulfate (100 ug/ml) and Trimethoprim (100 ug/ml) Example 29: | BS $1.8 \times 10^4$ XLD $9.0 \times 10^3$ | Found dead on day 5 | | | |
| Polymyxin B Sulfate (100 ug/ml) Example 30: | BS $2.1 \times 10^8$ XLD $1.8 \times 10^8$ | BS $6.3 \times 10^3$ XLD $5.3 \times 10^3$ | BS $2.5 \times 10^6$ XLD $2.3 \times 10^6$ | Found dead on day 9 | |
| Trimethoprim (250 ug/ml) Example 31: | BS * XLD * | Found dead on day 6 | | | |
| Control | BS $3.3 \times 10^4$ XLD * | BS $9.4 \times 10^6$ XLD $9.2 \times 10^4$ | BS * XLD * | BS $3.0 \times 10^6$ XLD $6.4 \times 10^5$ | SC(+) Tet(+) |

*Fecal sample could not be expressed

Each of the following examples 32–34 represents a pooled fecal sample from three chicks, each of which was placed into a separate solid bottom cage. Examples 32–34 reflect experiments conducted at the same time and in the proximity of examples 20–23. Hence examples 21–23 and 32–34 share the same control group, example 20. Each of the birds of examples 32–34 was inoculated orally on Day 1 with 0.5–1 of an S. enteritidis solution containing about $10^8$ CFU/ul. The antimicrobial solutions were supplied on Day 4. The fecal samples of day 4 were expressed prior to antimicrobial introduction.

As with examples 24–31, examples 32–34 of Table 6 show that it is more difficult to remove S. enteritidis infections from poultry than it is to inhibit such infections. However, example 33 indicates that trimethoprim may suppress S. enteritidis infections as the fecal samples from these chicks on Days 5 and 7 contained 10,000 to 60,000 colony forming units per gram in contrast to the 470,000 to 100,000,000 colony forming units per gram of fecal sample of the control group.

TABLE 6

GROUP II: Removal of S. enteritidis in Poultry

| Antimicrobial Concentration in Drinking Water Supply | Number of colony forming units per gram of chick fecal sample as determined with Bismuth Sulfide, XLD, and Brilliant Green agars, and presence or absence of S. enteritidis as determined with selenite Cystine and Tetrathionate Broth enrichments. | | | | |
|---|---|---|---|---|---|
| | Day 4 | Day 5 | Day 6 | Day 7 | Day 11 |
| Example 20 (Control) (No antimicrobials) | BS $2.3 \times 10^3$ XLD $1.8 \times 10^3$ BG $2.5 \times 10^3$ | BS $4.4 \times 10^4$ XLD $3.5 \times 10^4$ BG $4.9 \times 10^4$ [$4.7 \times 10^5$]* | BS $>10^4$ XLD $>8.00 \times 10^6$ BG $>10^4$ [$>2 \times 10^7$] | BS $8.0 \times 10^7$ XLD $2.2 \times 10^7$ BG $4.0 \times 10^7$ [$1.7 \times 10^8$] | BS SC(+) Tet(+) XLD SC(+) Tet(+) BG SC(+) Tet(+) |
| Example 31 Polymyxin B Sulfate (100 ug/ml) | BS $1.6 \times 10^3$ XLD $6 \times 10^2$ BG $2 \times 10^2$ | BS $3.5 \times 10^4$ XLD $1.9 \times 10^4$ BG $3.0 \times 10^4$ [$7.3 \times 10^5$] | | BS $2.2 \times 10^7$ XLD $1.6 \times 10^6$ BG $1.35 \times 10^7$ [$9 \times 10^7$] | |
| Example 32 Polymxin B Sulfate (100 ug/ml) and Trimethoprim (250 ug/ml) | BS $12 \times 10^3$ XLD $1 \times 10^3$ BG $1.2 \times 10^3$ | | BS $>10^4$ XLD $>8.50 \times 10^6$ BG $>10^4$ [$>8 \times 10^7$] | BS $2.10 \times 10^7$ XLD $6.2 \times 10^6$ BG $2.00 \times 10^7$ [$2.1 \times 10^8$] | BS $2.1 \times 10^4$ XLD $3.6 \times 10^3$ BG $1.4 \times 10^4$ [$1.0 \times 10^5$] |
| Example 33 Trimethoprim (250 ug/ml) | BS $1.1 \times 10^3$ XLD 0 BG $3 \times 10^2$ | BS $7 \times 10^2$ XLD $3.7 \times 10^2$ BG $8 \times 10^2$ [$1.6 \times 10^4$] | | BS $3.7 \times 10^3$ XLD $2.6 \times 10^3$ BG — [$5.6 \times 10^4$] | BS $5.0 \times 10^5$ XLD — BG $1.1 \times 10^5$ |
| | Day 13 | | Day 15 | | Day 19 |
| Example 20 (Control) (No antimicrobials) | BS SC(+) Tet(+) XLD SC(+) Tet(+) BG SC(+) Tet(+) | | BS $1.2 \times 10^4$ XLD $1.8 \times 10^4$ BG — [$4.4 \times 10^4$] | | BS SC(+) Tet(+) XLD SC(+) Tet(+) BG SC(+) Tet(+) |

TABLE 6-continued

GROUP II: Removal of *S. enteritidis* in Poultry

| Antimicrobial Concentration in Drinking Water Supply | Number of colony forming units per gram of chick fecal sample as determined with Bismuth Sulfide, XLD, and Brilliant Green agars, and presence or absence of *S. enteritidis* as determined with selenite Cystine and Tetrathionate Broth enrichments. | | |
|---|---|---|---|
| Example 31 | | | |
| Polymyxin B Sulfate (100 ug/ml) | BS $3.1 \times 10^3$<br>XLD $3.3 \times 10^3$<br>BG $2.7 \times 10^3$<br>[$4.6 \times 10^4$] | BS $1.0 \times 10^5$<br>XLD $9 \times 10^4$<br>BG —<br>[$3.9 \times 10^5$] | BS $1 \times 10^2$<br>XLD $1 \times 10^2$<br>BG —<br>[$2.9 \times 10^2$] |
| Example 32 | | | |
| Polymyxin B Sulfate (100 ug/ml) and Trimethoprim (250 ug/ml) | BS $8.8 \times 10^3$<br>XLD $6.9 \times 10^3$<br>BG $7.0 \times 10^3$<br>[$7.7 \times 10^4$] | BS $2.00 \times 10^5$<br>XLD $1.48 \times 10^5$<br>BG $1.7 \times 10^5$<br>[$1.1 \times 10^6$] | BS $1.2 \times 10^3$<br>XLD $4 \times 10^2$<br>BG $8 \times 10^2$<br>[$6.3 \times 10^3$] |
| Example 33 | | | |
| Trimethoprim (250 ug/ml) | BS $8.5 \times 10^3$<br>XLD $7.2 \times 10^3$<br>BG $6 \times 10^3$<br>[$6.1 \times 10^4$] | BS $2.9 \times 10^3$<br>XLD $2.6 \times 10^3$<br>BG $4.3 \times 10^3$<br>[$1.7 \times 10^4$] | BS $1.0 \times 10^3$<br>XLD $7 \times 10^2$<br>BG —<br>[$3.9 \times 10^3$] |

*Bracketed numbers represent average number of CFU/gm of fecal sample when dilution of the fecal sample is taken into account.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

What is claimed:

1. A method for controlling *S. enteritidis* in poultry comprising introducing orally a combination of trimethoprim and polymyxin into the poultry in an effective amount to control the *S. enteritidis* in the poultry.

2. The method according to claim 1, wherein the polymyxin and trimethoprim are introduced into the poultry via a consumable carrier supplied to the poultry to be introduced into the intestinal tract of the poultry, the polymyxin and the trimethoprim being dissolved in the carrier.

3. The method according to claim 1, wherein the trimethoprim and polymyxin are first introduced into poultry approximately 24 hours old and introduced daily thereafter for at least four days.

4. The method according to claim 1, wherein the trimethoprim and polymyxin are first introduced into poultry approximately 24 hours old and introduce daily thereafter for approximately at least 14 days whereupon the normal intestinal flora of the poultry has developed whereby the poultry is better equipped to handle infection.

5. The method according to claim 2, wherein the concentration of polymyxin is at least approximately 100 ug/ml in the carrier.

6. The method according to claim 2, wherein the concentration of trimethoprim is at least approximately 100 ug/ml in the carrier.

7. The method according to claim 2, wherein the concentration of trimethoprim is at least approximately 250 ug/ml in the carrier.

8. The method according to claim 2, wherein the concentration of trimethoprim and polymyxin in the carrier is at least approximately 250 ug/ml and 100 ug/ml, respectively.

9. The method according to claim 1, wherein the polymyxin comprises polymyxin B.

* * * * *